United States Patent [19]

Hergenrother et al.

[11] Patent Number: 5,268,439
[45] Date of Patent: Dec. 7, 1993

[54] TIN CONTAINING ELASTOMERS AND PRODUCTS HAVING REDUCED HYSTERESIS PROPERTIES

[75] Inventors: William L. Hergenrother; Tristram W. Bethea, both of Akron; John M. Doshak, Mogadore, all of Ohio

[73] Assignee: Bridgestone/Firestone, Inc., Akron, Ohio

[21] Appl. No.: 636,961

[22] Filed: Jan. 2, 1991

[51] Int. Cl.$^5$ .................. C08F 4/58; C08F 36/04; C08K 3/04
[52] U.S. Cl. .................. 526/340; 526/176; 526/190; 526/335; 524/571; 524/572; 524/575; 525/248; 525/331.9; 525/332.3; 525/332.9; 525/370; 525/375; 502/152; 152/564
[58] Field of Search .......... 526/176, 190, 336, 335, 526/340; 524/571, 572, 575; 525/248, 370, 375, 332.3, 332.9, 331.9; 152/564

[56] References Cited

U.S. PATENT DOCUMENTS

| | | | |
|---|---|---|---|
| 3,177,190 | 4/1965 | Hsieh | 260/94.2 |
| 3,317,918 | 5/1967 | Foster | 260/83.7 |
| 3,393,182 | 7/1968 | Trepka | 260/79.5 |
| 3,426,006 | 2/1969 | Nützel et al. | 260/83.8 |
| 3,439,049 | 4/1969 | Trepka | 260/624 |
| 3,856,877 | 12/1974 | Otsuki et al. | 260/677 |
| 4,015,061 | 3/1977 | Schulz et al. | 526/54 |
| 4,026,865 | 5/1977 | Uraneck et al. | 260/42.32 |
| 4,085,265 | 4/1978 | Otsuki et al. | 526/49 |
| 4,247,418 | 1/1981 | Halasa et al. | 252/431 |
| 4,278,781 | 7/1981 | Caspari et al. | 526/150 |
| 4,414,372 | 11/1983 | Farnham et al. | 526/190 |
| 4,429,091 | 1/1984 | Hall | 526/181 |
| 4,476,240 | 10/1984 | Hall et al. | 502/155 |
| 4,478,953 | 10/1984 | Yuki et al. | 502/155 |
| 4,614,771 | 9/1986 | Watanabe et al. | 525/351 |
| 4,616,069 | 10/1986 | Watanabe et al. | 525/370 |
| 4,736,003 | 4/1988 | Schneider et al. | 526/190 |
| 4,894,409 | 1/1990 | Shimada et al. | 524/492 |
| 4,914,147 | 4/1990 | Mouri et al. | 524/495 |

FOREIGN PATENT DOCUMENTS

| | | |
|---|---|---|
| 0067111 | 12/1982 | European Pat. Off. . |
| 0264506 | 4/1988 | European Pat. Off. . |
| 0282437 | 9/1988 | European Pat. Off. . |
| 0290883 | 11/1988 | European Pat. Off. . |
| 0316255 | 5/1989 | European Pat. Off. . |
| 138070 | 10/1979 | Fed. Rep. of Germany . |
| 247455 | 7/1987 | German Democratic Rep. . |
| 1025118 | 4/1966 | United Kingdom ......... 526/176 |
| 2117778 | 10/1983 | United Kingdom . |

OTHER PUBLICATIONS

Chemical Abstracts, vol. 86, No. 10 dated Mar. 7, 1977; T. Aikawa, Author; "Pressure-sensitive adhesives", published by American Chemical Society; p. 21, abstract No. 55967b.

Chemical Abstracts, vol. 94, No. 6 dated Feb. 9, 1981; B. I. Tarunin, et al, Author; "Molecular complexes of trialkyltin chloride and chloro(dialkyl) tin hydroperoxide as initiators of vinyl monomer polymerization", published by American Chemical Society; p. 15, abstract No. 31 282p.

"A Bifunctional Anionic Initiator Soluble in Non-Polar Solvents", Makromol. Chem. 179, 1978, pp. 551-555, by Beinert, et al.

"Bifunctional Anionic Initiators: A Critical Study and Overview", Makromol. Chem. 1986, 1985, pp. 2017-2024, by Bandermann, et al.

(List continued on next page.)

Primary Examiner—Fred Teskin
Attorney, Agent, or Firm—Daniel N. Hall

[57] ABSTRACT

An anionic polymerization initiator comprising the reaction product of a an organatin halide and lithium in a suitable solvent. Elastomeric polymers prepared with these initiators have tin containing functional groups on substantially every polymer chain and provide vulcanizable rubber compounds exhibiting reduced hysteresis. Articles such as tires, produced with low hysteresis elastomeric polymers have lower rolling resistance. Methods are also provided for preparing the initiators and the elastomers having reduced hysteresis properties.

26 Claims, No Drawings

OTHER PUBLICATIONS

"Anionic Polymerization Initiators Containing Protected Functional Groups and Functionally Terminated Diene Polymers", Journal of Polymer Science, Polymer Chemistry Edition, Vol. 12, pp. 153–166, by Schulz (1974).

"Specific Functionalization of Polymers by Carboxyl Groups", Makromol. Chem. 179, 1978, pp. 1383–1386, by Broze, et al.

"3-Dimethylaminopropyl-Lithium—An Analytical and Kinetic Investigation of a New Initiator System for Polymer Synthesis", European Polymer Journal, vol. 11, 1975, pp. 699–704, by Eisenbach, et al.

"The Organic Chemistry of Tin", Interscience Publishers, 1971, by Wilhelm P. Neumann.

"Preparation of Some Trialkyltin-lithium Compounds", J. Am. Chem. Soc., 75, 2507–2508 (1953) by Gillman and Rosenberg.

"Preparation and Reactions of Trialkyltin-lithium", J. Org. Chem, 28, 237–239 (1963), by Tamborski, Ford and Soloski.

"Some Reactions of Tributyl- and Triphenyl-stannyl Derivatives of Alkali Metals", J. Chem. Soc., 1961, 618–622 by Blake, Coates and Tate.

"New Perfectly Difunctional Organolithium Initiators for Block Copolymers Synthesis: Synthesis of dilithium initiators in the absence of polar additives", Polymer, vol. 22, Dec. 1981, p. 1724, by Guyot, et al.

"Polymerization of Unsaturated Compounds in the Presence of Lithium Diethylamide" by Vinogradov et al, *Polymer Science USSR*, vol. 4, 1963.

"Anionic Polymerization Initiators Containing Protected Functional Groups" Journal of Polymer Science, vol. 15, 1977, pp. 2401–2410, by Schulz et al.

"Anionic Polymerization Initiated by Diethylamide in Organic Solvents" by Angood et al, Journal of Polymer Science, vol. 11, p. 2777 (1973).

*Chemical Abstracts*, vol. 91, No. 12, Sep. 1979.

"Anionic Polymerization" by Cheng, American Chemical Society Symposium Series 166, p. 513 (1981).

Kanga et al, "Makromolecules" 23, 1990, at pp. 4235–4240; 4241–4246.

"An Improved Synthesis of p-Dimethylaminophenyl-Lithium", Hallas et al., Chem. and Ind., May, 1969.

TIN CONTAINING ELASTOMERS AND PRODUCTS HAVING REDUCED HYSTERESIS PROPERTIES

TECHNICAL FIELD

The subject invention relates to the anionic polymerization of diene polymer and copolymer elastomers. More specifically, the present invention relates to polymerization employing a tin containing initiator, resulting in a plurality of polymer chains wherein substantially each chain has a tin containing end group derived from the initiator.

Diene polymers and copolymers, prepared according to the present invention, have reduced hysteresis characteristics. Articles such as tires, power belts and the like which are prepared from these polymers exhibit increased rebound, decreased rolling resistance and less heat build-up during mechanical stress operations.

BACKGROUND ART

In the art, it is desirable to produce elastomeric compounds exhibiting reduced hysteresis. Such elastomers, when compounded to form articles such as tires, power belts and the like, will show an increase in rebound, a decrease in rolling resistance and will have less heat build-up when mechanical stresses are applied.

The main source of hysteretic power loss has been established to be due to the section of the polymer chain from the last cross link of the vulcanizate to the end of the polymer chain. This free end cannot be involved in an efficient elastically recoverable process, and as a result, any energy transmitted to this section of the cured sample is lost as heat. It is known in the art that this type of mechanism can be reduced by preparing higher molecular weight polymers which will have fewer end groups. However, this procedure is not useful because processability of the rubber during the addition of compounding ingredients and during shaping operations decreases rapidly with increasing molecular weight.

Another method of reducing hysteresis has been to react a lithium endcapped elastomer with a tin chloride compound to give polymer chains with terminated tin. Tin has an affinity for carbon-black, which affinity reduces hysteresis by removing the effect of a free end. However, with a plurality of polymer chains, endcapping is an inefficient process that results in only about 50-80 percent of the total number of chains being capped with tin. While this method has provided a decrease in hysteresis, the large number of polymer chains without a tin endcap do nothing to reduce hysteresis. In addition, no method is known for endcapping both ends of substantially every polymer chain.

It is also known in the art to employ tin-containing organo-metal compounds as polymerization initiators. For instance, U.S. Pat. No. 3,426,006 discloses the catalyst lithium tributyl tin in diethyl ether for such a purpose. This initiator has been shown by Tamborshi et al, *Journal of Organic Chemistry*, volume 28, page 237 (1963) to be predominantly an equilibrium mixture of dibutyltin and butyl lithium wherein the butyl lithium is the more active initiator and hence, the polymer chains produced from its initiation actually contain little or no tin atoms. Thus, heretofore, the art has not shown a means whereby substantially each polymer chain of an elastomer can be provided with a tin end group resulting from the initiator.

The present invention provides novel initiators for anionic polymerization, which initiators provide polymer chains having an end group containing a tin atom. The tin containing end group provides the polymer chain with a functional group which can strongly interact with carbon black to (a) provide an elastically efficient end group and (b) greatly improve the dispersability of carbon black throughout the elastomeric composition during compounding. Further, the present invention also provides for polymer chains as above, having another tin atom at the other end of the chains.

DISCLOSURE OF THE INVENTION

It is therefore, an object of the present invention to provide anionic polymerization initiators which promote the incorporation of functional tin groups in the polymer chain.

It is a further object of the present invention to provide a method of preparing an anionic polymerization initiator.

It is another object of the present invention to provide elastomers having reduced hysteresis properties.

It is yet another object of the present invention to provide elastomers having a plurality of polymer molecules wherein substantially each molecule has a tin atom.

It is still another object of the present invention to provide elastomers having a plurality of polymer molecules wherein substantially each molecule has a tin containing end group on the initiating end, wherein the molecules may be terminated with a second tin-containing group or other functional group known to provide similar properties.

It is another object of the present invention to provide a method of preparing an elastomer having a plurality of polymer molecules wherein substantially each molecule has a tin atom.

It is also an object of the present invention to provide diene polymers and copolymers having reduced hysteresis characteristics.

It is a further object of the present invention to provide vulcanizable elastomeric compounds having reduced hysteresis properties.

Still another object of the present invention is to provide an improved tire having decreased rolling resistance.

These and other objects together with the advantages thereof over the existing art, which shall become apparent from the specification which follows, are accomplished by the invention as hereinafter described and claimed.

In general, an anionic polymerization initiator comprises the reaction product of from about 93 to about 99 percent by weight of an organotin compound selected from the group consisting of triorgano substituted-tin halide compounds and hexaorgano substituted di-tin compounds having a tin-tin bond, and from about 1 to about 7 percent by weight of lithium metal. The reaction is carried out in the presence of a suitable solvent.

A method of preparing an anionic polymerization initiator comprises the step of reacting from about 93 to about 99 percent by weight of an organotin compound selected from the group consisting of triorgano substituted-tin halide compounds and hexaorgano substituted di-tin compounds having a tin-tin bond, with from about 1 to about 7 percent by weight of lithium in the presence of a suitable solvent.

The invention also provides an elastomer having reduced hysteresis properties comprising a plurality of polymer molecules wherein substantially each polymer molecule contains at least one tin atom and a lithium atom prior to quenching.

An elastomer having reduced hysteresis properties is provided and is made by anionically polymerizing a monomer solution containing at least one monomer selected from the group consisting of conjugated diene monomers having from about 4 to 12 carbon atoms, vinyl aromatic monomers having from about 8 to 18 carbon atoms and mixtures thereof, in the presence of an organic initiator containing tin. Substantially each polymer molecule of the elastomer contains a tin atom derived from the organic initiator.

A method of preparing an elastomer is also provided and comprises the steps of forming a solution of one or more anionically polymerizable monomers in a solvent and polymerizing the monomers in the presence of an organotin lithium initiator. The elastomer comprises a plurality of polymer molecules with substantially each molecule having a tin atom on one end and a lithium atom on the other end, prior to termination.

A vulcanizable elastomeric compound having reduced hysteresis properties is also provided and comprises an elastomer comprising a plurality of polymer molecules wherein substantially each polymer molecule contains at least one tin atom and a lithium atom prior to quenching. The compound also comprises from about 20 to about 100 parts by weight of carbon black, per 100 parts of the elastomer.

An improved tire having decreased rolling resistance is also provided, and results from a treadstock containing a vulcanizable elastomeric compound comprising an elastomer. The elastomer comprises a plurality of polymer molecules wherein substantially each polymer molecule contains at least one tin atom and a lithium atom prior to quenching. The compound also comprises from about 20 to about 100 parts by weight of carbon black, per 100 parts of the elastomer.

PREFERRED EMBODIMENT FOR CARRYING OUT THE INVENTION

As will become apparent from the description which follows, the present invention provides novel elastomeric compounds having a plurality of polymer chains wherein substantially all of the chains are provided with a tin containing, functional end group. It has been discovered herein that vulcanizable elastomeric compounds and articles thereof based upon such functionally terminated polymers exhibit useful properties, particularly the property of reduced hysteresis. When compounded to make products such as tires, power belts and the like, these vulcanizable elastomeric compounds exhibit increased rebound, decreased rolling resistance and less heat build-up during periods of applied mechanical stress.

In order to provide a tin containing end group on substantially every polymer chain, the present invention makes use of a tin containing initiator. The initiator, according to the present invention, is the reaction product of a triorgano substituted-tin halide or a hexaorgano substituted di-tin compound with lithium metal in the presence of a suitable solvent. Preferred is a triorgano substituted-tin halide has the general formula $R_3SnX$. The organic moiety R is selected from the group consisting of alkyls having from about 1 to about 20 carbon atoms, cycloalkyls having from about 3 to about 20 carbon atoms, aryls having from about 6 to about 20 carbon atoms and aralkyls having from about 7 to about 20 carbon atoms. Typical alkyls include n-butyl, s-butyl, methyl, ethyl, isopropyl and the like. The cycloalkyls include cyclohexyl, menthyl and the like. The aryl and aralkyl groups include phenyl, benzyl and the like.

The initiators according to the present invention may also be produced by other means. For example, the initiator may be formed as the reaction product of a hexaorgano-substituted di-tin compound $R_3SnSnR_3$ containing a tin-tin bond, with lithium metal (where R is as described hereinabove). Preferred di-tin compounds have between 6 and 120 carbon atoms, such as hexabutyldi-tin.

It is preferred that the initiators according to the present invention are the reaction product of from about 93 to about 99 percent by weight of an organotin compound and from about 1 to about 7 percent by weight of lithium.

The halide constituent X of the triorgano substituted-tin halide includes chlorides and bromides. Lithium is preferably present as a reactant in the form of lithium metal, and may also be present as a dispersion in mineral oil. Preferably, the solvent employed is tetrahydrofuran, tetramethylethylenediamine, or diethylene methyl ether (diglyme). Some other solvents such as polar organic ethers, tertiary amines, dimethyl ether, diethyl ether and tributylamine, have been employed with unsatisfactory results, in that either the reaction does not go to completion or the trialkyl tin initiator reacts with the solvent. Not going to completion means that the reaction of the tin chloride compound with lithium metal gave less than appreciable amounts of the desired tin lithium compound with the predominant product being the intermediate hexaorgano substituted di-tin stage or no reaction at all.

The desired reaction product of the triorgano substituted-tin halide and the lithium is a triorgano substituted-tin lithium compound. The preferred initiator has the general formula $R_3SnLi$, where R is as defined hereinabove. One preferable catalyst is the reaction product of tributyl tin chloride and lithium metal in tetrahydrofuran, forming tributyl tin lithium.

As stated above, the initiator thus formed may be employed as an initiator to prepare any anionically-polymerized elastomer, e.g., polybutadiene, polyisoprene and the like, and copolymers thereof with monovinyl aromatics such as styrene, alpha methyl styrene and the like, or trienes such as myrcene. Thus, the elastomers include diene homopolymers and copolymers thereof with monovinyl aromatic polymers. Suitable monomers include conjugated dienes having from about 4 to about 12 carbon atoms and monovinyl aromatic monomers having 8 to 18 carbon atoms and trienes. Examples of conjugated diene monomers and the like useful in the present invention include 1,3-butadiene, isoprene, 1,3-pentadiene, 2,3-dimethyl-1,3-butadiene and 1,3-hexadiene, and aromatic vinyl monomers include styrene, a-methylstyrene, p-methylstyrene, vinyltoluene and vinylnaphtalene. The conjugated diene monomer and aromatic vinyl monomer are normally used at the weight ratios of 95-50:5-50, preferably 95-65:5-35.

Polymerization is usually conducted in a conventional solvent for anionic polymerizations such as hexane, cyclohexane, benzene and the like. Other techniques for polymerization, such as semi-batch and continuous polymerization may be employed. In order to promote randomization in copolymerization and to control vinyl content, a polar coordinator may be added to the polymerization ingredients. Amounts range between 0 and 90 or more equivalents per equivalent of lithium. The amount depends on the amount of vinyl desired, the level of styrene employed and the temperature of the polymerization, as well as the nature of the specific polar coordinator (modifier) employed.

Compounds useful as polar coordinators are organic and include tetrahydrofuran, linear and cyclic oligomeric oxolanyl alkanes such as 2-2'-di(tetrahydrofuryl) propane, di-piperidyl ethane, hexamethylphosphoramide, N-N'-dimethylpiperazine, diazabicyclooctane, dimethyl ether, diethyl ether, tributylamine and the like. The linear and cyclic oligomeric oxolanyl alkane modifiers are described in U.S. Pat. No. 4,429,091, owned by the Assignee of record, the subject matter of which is incorporated herein by reference. Other compounds useful as polar coordinators include those having an oxygen or nitrogen hetero-atom and a non-bonded pair of electrons. Examples include dialkyl ethers of mono and oligo alkylene glycols; "crown" ethers; tertiary amines such as tetramethylethylene diamine (TMEDA); tetrahydrofuran (THF), THF oligomers linear and the like.

A batch polymerization is begun by charging a blend of monomer(s) and solvent to a suitable reaction vessel, followed by the addition of the polar coordinator (if employed) and the initiator compound previously described. The reactants are heated to a temperature of from about 20° to about 200° C., and the polymerization is allowed to proceed for from about 0.1 to about 24 hours. A tin atom is derived from the initiator compound and attaches at the initiation site. Thus, substantially every resulting polymer chain has the following general formula

R$_3$SnYLi where R is as described above, the tin atom is derived from the polymerization initiator, and Y is a divalent polymer radical which is derived from any of the foregoing diene homopolymers, monovinyl aromatic polymers, diene/monovinyl aromatic random copolymers and block copolymers. The monomer addition at the lithium end causes the molecular weight of the polymer to increase as the polymerization continues.

To terminate the polymerization, and thus control polymer molecular weight, a terminating agent may be employed. Active hydrogen compounds such as water or alcohol can be used, or compounds providing terminal functionality (i.e., "endcapping") can be used such as tin tetrachloride, R$_3$SnCl, R$_2$SnCl$_2$, RSnCl$_3$, carbodiimides, N-methylpyrrolidine, cyclic amides, cyclic ureas, isocyanates, Schiff bases, 4,4'-bis(diethylamino) benzophenone, and the like, where R is as described hereinabove. The terminating agent is added to the reaction vessel, and the vessel is agitated for about 1 to about 1000 minutes. Preferably, the terminating agent is a tin containing compound suitable for use as a terminator, such as tin tetrachloride or tributyl tin chloride. The chlorine on the tin reacts with the lithium end group of the resulting polymer chain, forming a polymer having the following general formula where R and Y are as previously described:

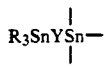

R$_3$SnYSn—

As a result, an elastomer is produced having an even greater affinity for compounding materials such as carbon black, and hence, even further reduced hysteresis. With the tin group at both ends of the polymer chain, the loss of some of the "living" end of the polymer due to inefficient endcapping (i.e., the side reactions of the lithium) is not a drawback in that the presence of the tin end group from the initiator produces much of the desired reduction in hysteresis regardless of the inefficiency of the endcapping at the living end. Further, it is to be appreciated that other terminating agents and/or procedures may be followed, and still fall within the scope of the present invention. For example, the polymers according to the invention may be coupled by using SnCl$_4$ (tin tetrachloride) as a terminating agent.

It will also be appreciated by one skilled in the art that the polymer chains of the present invention may be endcapped with non-tin endcapping agents, and that the resulting polymers are also within the scope of the invention. Examples of useful endcapping agents which do not contain tin, as well as further examples of tin-containing endcapping agents are found in U.S. Pat. No. 4,616,069 which is herein incorporated by reference. For instance, one preferred endcapping agent which does not contain tin is N,N'-dimethylethyleneurea.

The polymer may be separated from the solvent by conventional techniques. These include steam or alcohol coagulation, thermal desolventization, or any other suitable method. Additionally, solvent may be removed from the resulting polymer by drum drying, extruder drying, vacuum drying or the like.

The elastomers of the present invention comprise a plurality of polymers, having at least one tin containing end group on substantially each polymer molecule or "chain", and if terminated with a suitable tin containing terminating agent, a tin group on both ends of the chain. Furthermore, as will be appreciated by one skilled in the art, a tetra functional tin molecule may also be used to produce a tin coupled product. As noted hereinabove, the tin containing end groups have an affinity for compounding materials such as carbon black. Such compounding results in products exhibiting reduced hysteresis, which means a product having increased rebound, decreased rolling resistance and has less heat build-up when subjected to mechanical stress.

The polymers of the present invention can be used alone or in combination with other elastomers to prepare the tire treadstock compounds. For example, they can be blended with any conventionally employed treadstock rubber which includes natural rubber, synthetic rubber and blends thereof. Such rubbers are well known to those skilled in the art and include synthetic polyisoprene rubber, styrene/butadiene rubber (SBR), polybutadiene, butyl rubber, Neoprene, ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like. When the polymers of the present invention are blended with conventional rubbers, the amounts can vary widely such as between 10 and 99 percent by weight, depending upon the amount of hysteresis reduction desired.

The polymers can be compounded with carbon black in amounts ranging from about 20 to about 100 parts by weight, per 100 parts rubber (phr), with about 40 to about 70 phr being preferred. The carbon blacks may include any of the commonly available, commercially-produced carbon blacks but those having a surface area (EMSA) of at least 20 m$^2$/g and more preferably at least 35 m$^2$/g up to 200 m$^2$/g or higher are preferred. Surface area values used in this application are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the carbon black products of the invention. Typical values for surface areas of usable carbon blacks are summarized in the following Table I.

TABLE I

| Carbon Blacks | |
|---|---|
| ASTM Designation (D-1765-82a) | Surface Area (m$^2$/g) (D-3765) |
| N-110 | 126 |
| N-220 | 111 |
| N-339 | 95 |
| N-330 | 83 |
| N-550 | 42 |
| N-660 | 35 |

The carbon blacks utilized in the preparation of the rubber compounds of the invention may be in pelletized form or an unpelletized flocculant mass. Preferably, for more uniform mixing, unpelletized carbon black is preferred. The reinforced rubber compounds can be cured in a conventional manner with known vulcanizing agents at about 0.5 to about 4 phr. For example, sulfur or peroxide-based curing systems may be employed. For a general disclosure of suitable vulcanizing agents one can refer to Kirk-Othmer, *Encyclopedia of Chemical Technology*, 3rd ed., Wiley Interscience, N.Y. 1982, Vol. 20, pp. 365–468, particularly "Vulcanization Agents and Auxiliary Materials" pp. 390–402. Vulcanizing agents may be used alone or in combination.

Vulcanizable elastomeric compositions of the invention can be prepared by compounding or mixing the polymers thereof with carbon black and other conventional rubber additives such as fillers, plasticizers, antioxidants, curing agents and the like, using standard rubber mixing equipment and procedures and conventional amounts of such additives. Such elastomeric compounds when vulcanized using conventional rubber vulcanization conditions have reduced hysteresis properties and are particularly adapted for use as tread rubbers for tires having reduced rolling resistance.

General Experimental

In order to demonstrate the preparation and properties of elastomers prepared according to the present invention, a tin containing initiator was prepared by reacting tributyl tin chloride with lithium metal in tetrahydrofuran. A solution of styrene and butadiene monomers in hexane was prepared and was polymerized with the above described initiator. To further show the effectiveness of the invention, a similar monomer solution was polymerized with n-butyl lithium as an initiator to provide a comparative control example. Termination was carried out by reaction with isopropyl alcohol. Finally, samples of both polymers were also terminated with a tin containing terminating (endcapping) agent, namely, tributyl tin chloride. As noted above, various techniques known in the art for carrying out polymerizations may be employed without departing from the scope of the present invention. For example, the polymers according to the invention may be coupled by using SnCl$_4$ (tin tetrachloride) as a terminating agent.

All samples were then tested for tensile strength (psi), percent elongation, tan delta (at both 24° C. and 65° C.), and the change in tan delta as compared to a control polymer was calculated. Polymers 1 and 5 were chosen as the controls from which the change in tan delta was calculated because of their tin-free nature. Tan delta was determined on a Rheometrics stress rheometer at 0.5 Hz. Each compounded polymer was also tested for rebound by employing the industry standard ball drop test.

Initiator Preparation

A solution was prepared comprising 68 cc of dry, peroxide free tetrahydrofuran and 27.1 cc of neat (undiluted) tributyl tin chloride having a concentration of 3.69 moles/liter. To this was added 9.2 cc of a 20-30 percent mineral oil dispersion of lithium metal (0.2-0.3 moles of lithium), and the mixture was mixed gently for 20 hours. A temperature rise of over 50° C. was noted. A powder-like precipitate of lithium chloride was noted, plus a clear middle layer, and a top layer of unreacted lithium dispersion. The clear, yellow to dark green center layer, containing of tributyl tin lithium in tetrahydroduran, was isolated and used in the ensuing polymerizations according to the present invention. For comparison, control polymers were also prepared, as will be described hereinbelow. It is believed that lithium nitride is present in the tributyl tin lithium layer, and that the color range between yellow and dark green is dependent upon the amount of lithium nitride actually present. The lithium nitride formed by the reaction of the metallic lithium with gaseous N2 at ambient temperature.

Polymerization

Example No. 1 (Polymers 1 and 2)

To a 5 gal. reactor vessel was added 2295 grams of a 33% styrene in hexane blend (757.4 grams styrene) and 7893 grams of a 24.5% butadiene in hexane blend (1955.6 grams of butadiene). To the monomer blend was then added 30.0 millimoles (mM) butyl lithium catalyst and 25 mM of a modifier, namely 2-2'-di(tetrahydrofuryl) propane. The catalyst and modifier were charged to the reactor vessel at about 49° C. Prior to the catalyst addition, the monomer blend was found to contain an impurity level that would consume 4-8 mM of lithium catalyst. As a result, the charge of catalyst included an excess thereof needed to react with the impurities measured.

After about 3 hours at about 49° C., approximately one-half of the polymer cement (5000–5400 grams) was removed under pressure and added to isopropanol containing about 1% of dibutyl p-cresol (DBPC, an antioxidant), based upon the weight of the polymer collected. This sample was then desolventized by drum drying and used as a reference polymer (Polymer 1 in the Table I), to evaluate changes caused by the subsequent treatment of the remaining living lithium polymer in the reactor. Polymer 1 was found to have a Mn of 112,000 grams/mol, a vinyl polybutadiene content of 49 percent and a styrene content of 28 percent.

To the polymer remaining in the reactor was added 13.9 mM of 3.69 (neat) tributyltin chloride. After about 15 minutes, this tin terminated polymer (Polymer 2) was isolated in the same manner as Polymer 1 described hereinabove.

Example No. 2 (Polymers 3 and 4)

Another polymerization was conducted in a manner substantially similar to Example No. 1. In this example however, the catalyst charged was 30.0 mM of the tributyltin lithium described above, and the modifiers were 6.3 mM of 2-2'-di(tetrahydrofuryl) propane and 250 mM of tetrahydrofuran.

Again, after polymerization approximately one-half of the resulting polymer cement was removed and isolated, and is reported below as Polymer 3. The remaining polymer in the reactor was also tin terminated with 13.9 mM of tributyltin chloride, and is reported as Polymer 4. Polymer 3 was found to have an Mn of 109,000 grams/mol, a vinyl polybutadiene content of 37 percent and a styrene content of 30 percent.

Example No. 3 (Polymers 5 and 6)

Control polymers 5 and 6 were prepared in a substantially similar manner. The polymerization included 27.1 mM of butyl lithium catalyst and 270 mM of tetrahydrofuran, in place of the catalyst/modifier charges described with the previous examples. One-half of the resulting polymer was isolated as Polymer 5, and the remaining half was tin terminated with 14.9 mM of tributyl tin chloride, Polymer 6. Polymer 5 was determined to contain 30 percent vinyl polybutadiene and 26 percent styrene. Mn was found to be 90,500 grams/mol.

Example No. 4 (Polymers 7 and 8)

A fourth polymerization was conducted as above, and included a catalyst charge of 36.2 mM of tributyl tin lithium and 370 mM of tetrahydrofuran as a modifier. One-half the resulting polymer was isolated as Polymer 7, and the remaining half was tin terminated with 14.9 mM of tributyltin chloride, Polymer 8. The Mn of Polymer 7 was found to be 79,400 grams/mol, and the polymer contained 31 percent vinyl polybutadiene and 28 percent styrene.

The eight polymers 1–8, were then compounded with normal compounding materials. To 100 parts by weight of each polymer was added 50 parts of ASTM N339 carbon black, 3 parts of zinc oxide and 1 part of p-phenylenediamine to provide 154 parts of a masterbatch. The masterbatch was then mill mixed with 1.8 parts of sulfur, 2.0 parts of stearic acid and 1.0 parts of Santocure NS. The rubber compounds were cured at 150° C. for 30 minutes.

The physical test results for Polymers 1–4 are reported in Table II, and the results for Polymers 5–8 are reported in Table III. Polymers 1 and 5 were chosen as the controls from which the change in tan delta was calculated because of their tin-free nature.

TABLE II

Hysteresis Properties of Rubber Compounds Containing Polymer 1-4

| Compound Containing | Control Polymer 1 | Control Polymer 2 | Invention Polymer 3 | Invention Polymer 4 |
|---|---|---|---|---|
| Polymer Initiator | BuLi[c] | BuLi[c] | Bu$_3$SnLi[e] | Bu$_3$SnLi[e] |
| Endcapping agent | None | Bu$_3$SnCl[d] | None | Bu$_3$SnCl[d] |
| Tensile (psi) | 2493 | 2390 | 2381 | 2888 |
| ML$_{1+4}$(100° C.) | 65.5 | 66.7 | 97.5 | 99.4 |
| Compound | | | | |
| % Elongation[a] | 290 | 297 | 277 | 298 |
| Rebound | 32.8 | 35.2 | 48.0 | 49.8 |
| tan δ | | | | |
| 24° C. | .1938 | .1764 | .1301 | .1228 |
| 65° C. | .1375 | .1245 | .08815 | .07237 |
| % Δ tan δ[b] | | | | |
| 24° C. | — | −8.98 | −32.9 | −36.6 |
| 65° C. | — | −9.46 | −35.9 | −40.1 |

[a]percent elongation at break
[b]change from Polymer 1
[c]butyl lithium
[d]tributyltin chloride
[e]tributyltin lithium

TABLE III

Hysteresis Properties of Rubber Compounds Containing Polyers 5-8

| Compound Containing | Control Polymer 5 | Control Polymer 6 | Invention Polymer 7 | Invention Polymer 8 |
|---|---|---|---|---|
| Polymer Initiator | BuLi[c] | BuLi[c] | Bu$_3$SnLi[e] | Bu$_3$SnLi[e] |
| Endcapping agent | None | Bu$_3$SnCl[d] | None | Bu$_3$SnCl[d] |
| Tensile (psi) | 3040 | 3536 | 2262 | 3407 |
| ML$_{1+4}$(100° C.) | 69.8 | 94.6 | 90.7 | 109 |
| Compound | | | | |
| % Elongation[a] | 352 | 347 | 276 | 277 |
| Rebound | 45.6 | 49.2 | 54.3 | 54.6 |
| tan δ | | | | |
| 24° C. | .1954 | .1559 | .1167 | .1084 |
| 65° C. | .1590 | .1076 | .0938 | .0773 |
| % Δ tan δ[b] | | | | |
| 24° C. | — | −20.2 | — | −7.11 |
| 65° C. | — | −37.3 | — | −17.16 |
| % Δ tan δ[b] | | | | |
| 24° C. | — | −20.2 | −40.3 | −44.5 |
| 65° C. | — | −37.3 | −41.0 | −51.4 |

[a]percent elongation at break
[b]change from Polymer 5
[c]butyl lithium
[d]tributyltin chloride
[e]tributyltin lithium With respect to the data reported in Table II, it is noted that the compounds containing Polymers 3 and 4, according to the present invention, showed a percent rebound of 48.0 and 49.8 respectively. This is a considerable improvement over the control compounds containing Polymers 1 and 2, which showed percent rebounds of 32.8 and 35.2 respectively. The improvement in rebound would suggest a corresponding decrease in tan delta, which was confirmed by the tan delta data.

At both 24° C. and 65° C. tests, tan delta for the compounds containing Polymers 3 and 4 according to the invention was found to be superior to that of the compounds containing Polymers 1 and 2. The lower the tan delta number, the lower are the hysteresis properties of the sample.

These data show that Polymers 3 and 4, both of which were prepared according to the invention by employing the reaction product of the organo tin halide and lithium as an initiator, provided the result of a reduction in hysteresis in the elastomeric compound.

Similarly, with respect to the data reported in Table III, the compounds containing Polymers 7 and 8 according to the invention showed percent rebounds of 54.3 and 54.6 respectively. Polymers 5 and 6 prepared without a tin-containing initiator, showed rebound percents of 45.6 and 49.2 respectively.

Again, the hysteresis data showed that the polymers according to the invention, Polymers 7 and 8, were superior to Polymers 5 and 6. For example, a tan δ reduction of between 40–50 percent was found between Polymers 7 and 8 of the invention as compared to the control, Polymer 5.

Example No. 5

In order to demonstrate the practice of the present invention with a different organotin halide, 47 milliliters (mL) of tetrahydrofuran containing 9.64 grams (25 mM) of triphenyltin chloride was added to 2.4 mL of a 21.4M lithium dispersion in mineral oil (52.4 mM of lithium). After gently stirring for 16 hours, lithium chloride precipitated out, excess lithium floated to the top, and a dark green-black middle layer solution was isolated.

The middle layer, containing triphenyltin lithium, was used as an initiator to polymerize butadiene monomer. To 394 grams of a 24.5 percent butadiene in hexane solution (96.5 grams of monomer) was added 4.81 mL of the prepared and isolated catalyst. The polymerization was allowed to continue for 4 hours at 50° C. The polymer that was produced was tested by size exclusion chromatography (GPC), with ultraviolet and refractive index detectors. A strong ultraviolet absorption at the same retention volume as the refractive index peak maximum was found. This indicated that the triphenyltin end group was attached to substantially each polymer chain. The polymer was also shown to be 17.8 percent cis, 25.2 percent trans and 57 percent vinyl polybutadiene.

Example No. 6

Another polymerization was conducted using tetramethylethylenediamine (TMEDA) as a solvent. To a solution of 13.65 mL of tributyltin chloride (50 mM) in 33 mL of neat 6.62M TMEDA was added 2.3 mL of a lithium dispersion in mineral oil (71 mM of lithium). The reaction was cooled to limit the temperature to 55° C., and after 1 hour an additional 31 mM of lithium dispersion was added and the reaction was continued for another 3 hours. A large precipitate of LiCl was formed from the green solution which had a small amount of lithium metal dispersion floating on the surface.

To 420 grams of a 24.5 percent butadiene blend in hexane (102.9 grams of butadiene) was added 1.72 mL of the above catalyst free of any solids. The solution immediately turned orange and after 18 hours at 50° C. gave a polybutadiene. Analysis showed the polymer to be 76.8 percent vinyl, 8.4 percent cis and 14.8 percent trans with a GPC molecular weight of 95,000 grams/mol.

Example No. 7

To demonstrate the practice of the present invention with a di-tin compound, tributyltin lithium was prepared from hexabutyldi-tin as follows.

To a 6 ounce beverage bottle, previously baked at 120° C. overnight, capped with a rubber lined crown cap, cooled to room temperature under nitrogen, and flushed with argon, was added 1.5 mL of a 30 percent dispersion of lithium in mineral oil (52 mM lithium), 15 mL tetrahydrofuran, and 5.05 mL (10 mM) hexabutylditin. The mixture was gently agitated for 18 hours at 60° C. After the excess lithium floated to the top, 1.44 mL of the clear dark green-brown solution was allowed to react at 50° C. with 71.8 grams of butadiene in a hexane solution in a 28 ounce beverage bottle treated as described hereinabove. Upon completion of the polymerization, the reaction was terminated with isopropanol, antioxidant was added, and the solution was dried. By size exclusion chromatography, the polymer Mn was found to be 119,900 and infrared showed a vinyl content of 36.0 percent.

As a comparison, an initiator was made in a similar manner from 1.5 mL (52 mM) lithium dispersion and 5.42 mL (20 mM) tributyltin chloride in 15 mL tetrahydrofuran. This reaction was very fast and exothermic. After the lithium separated, 1.35 mL of the clear dark green-brown solution was allowed to react with 67.6 grams butadiene in a hexane solution as described hereinabove. The polymer Mn was found to be 78,000 and the vinyl content was 37.0 percent.

Example No. 8 (Polymer 9)

As stated hereinabove, the polymers formed according to the present invention may be coupled with SnCl₄, tin tetrachloride. The following example shows such a procedure.

To a 2 gallon reactor was added 694 grams of a 33 percent styrene solution in hexane (229 grams of styrene), 3638 grams of a 25.2 percent butadiene solution in hexane (917 grams of butadiene), and 0.88 mL of a 1.61M solution of butyl lithium in hexane to compensate for most of the reactor impurities. To this blend at 19° C. was then added 16.45 mL of a 0.613M solution of tributyltin lithium in tetrahydrofuran and 2.35 mL additional tetrahydrofuran. The temperature was gradually raised to 46° C. over three hours when a small sample was taken. To the remainder, 2.51 mL of 1.0M SnCl₄ in hexane was added over 15 minutes. The reaction was continued for 1 hour when the polymer was collected in isopropyl alcohol containing antioxidants and was drum dried. Proton nuclear magnetic resonance (nmr) analysis on the final polymer (Polymer 9) showed a styrene content of 20.5 percent with no block and a vinyl content of 53.0 percent. Gel permeation chromatography of the small sample gave an Mn of 142,000 and a dispersity of 1.18 while the Polymer 9 had a branched Mn of 259,000 and a dispersity of 1.93.

Example No. 9 (Polymer 10)

A similar polymer to that of Polymer 9 was made by initiating the polymerization of butadiene and styrene using quantities described in Example No. 8 hereinabove with 15.04 mL of 0.613M tributyltin lithium in tetrahydrofuran and 3.76 mL additional tetrahydrofuran. The temperature was gradually raised from 20° C. to 50° C. over three hours. After a small sample was taken, and the live polymer was coupled with 2.30 mL of 1.0M SnCl₄ in hexane over 15 minutes, the polymer was isolated in a manner similar to Polymer 9. Proton nmr analysis on the final polymer (Polymer 10) showed 20.6 percent styrene with no block and 51.4 percent vinyl. The GPC of the sample gave an Mn of 556,000 and a dispersity of 2.07.

Evaluation of Polymers and a Control Polymer 11

Polymers 9 and 10 were compounded in a test tread recipe comprising 100 parts rubber, 55 phr of ASTM N351 carbon black, 10 phr oil, 3 phr zinc oxide, 2 phr wax, 2 phr stearic acid, 1 phr antioxidant, 1.5 phr sulfur and 1 phr accelerator and cured for 35 minutes at 300° F. A stock made with tin-coupled styrene/butadiene rubber(Polymer 11), commercially available from Japan Synthetic Rubber Company, was used as a control. Selected properties of the polymers and the cured stocks are shown in the Table IV hereinbelow.

TABLE IV

| SnCl₄ Coupled Polymer Analysis | | | |
|---|---|---|---|
| Compound Containing | Invention Polymer 9 | Invention Polymer 10 | Control Polymer 11 |
| Styrene, % | 20.5 | 20.6 | 20.0 |
| Vinyl, % | 53.0 | 51.4 | 60.0 |
| ML₁₊₄(100° C.) Gum | 55 | 65 | 75 |
| 300% Modulus, psi | 2880 | 2730 | 2350 |
| Tensile, psi | 3200 | 3085 | 3210 |
| Maximum Elong., % | 370 | 376 | 431 |
| Tan δ, 23° C. | 0.1089 | 0.1071 | 1.1244 |
| Tan δ, 50° C. | 0.0759 | 0.0739 | 0.0901 |
| Pico abrasion (index) | 116 | 117 | 110 |

As is known in the art, the Pico abrasion is a measure of wear resistance as determined by a B.F. Goodrich Pico Abrasion Tester.

The improved wear resistance of products according to the present invention is shown by the Pico abrasion index of Polymers 9-11. Polymers 9 and 10 were found to have an index of 116 and 117 respectively, while the control stock made with the commercially available rubber (Polymer 11) had an index rating of 100.

Polymers 9-11 were coupled with tin tetrachloride. The styrene contents and the vinyl contents of each were comparable. The Mooney viscosity of Polymer 11 was the highest and the cured stock made from it has the highest tan δ values. Those skilled in the art will understand that, all other things being equal, tan δ at 50° C. is an indication of the rolling resistance of a tread while tan δ at 23° C. predicts the dry traction of the tread. The very low values of tan δ for compounds made from Polymers 9 and 10 and the significantly increased Pico abrasion indices must be attributed to the use of the tributyltin lithium initiator instead of butyl lithium. Although it was expected that some reduction in the tan δ values would result, the significantly lower tan δ values and the large improvement in wear properties imparted by these polymers were unexpected.

Comparative Tin Catalyst Examples

As was stated hereinabove, the preparation of a tributyltin lithium catalyst in diethyl ether, for use as a polymerization initiator is discussed in U.S. Pat. No. 3,426,006. In order to demonstrate the differences between such catalysts and the present invention, a series of the comparative polymerizations were performed with both catalysts.

Comparative Example I

A catalyst according to the teaching of U.S. Pat. No. 3,426,006 was prepared by making a slurry of 10.01 grams (52.8 mM) of pure stannous chloride in 23.58 grams (33.3 mL, 318.1 mM) of dry diethyl ether and then at 0° C. slowly adding 98.28 mL of 1.61M (152.8 mM) butyl lithium in hexane. The mixture slowly turned brown upon addition and after 16 hours at 0°-25° C. was shown by Gilman titration to have a 0.344M active lithium concentration. This solution was used to polymerize butadiene and to prepare a styrene/butadiene rubber for testing, as will now be described.

Polybutadiene was prepared by the addition of a 2 mM of the above described catalyst to 104 grams of butadiene monomer in a 24.5 percent hexane solution. The polymerization progressed at 50° C. for 16 hours to give a very viscous brown non-flowing cement (this viscosity is typical of the polymers prepared with a di-lithium catalyst). The addition of 3 mL of methanol reduced the viscosity to near the level expected from the charge of catalyst and monomer, without changing the color of the cement. This color was slowly lost when the cement was exposed to the air over the next 3 days. Analysis indicated 33.8 percent cis, 49.8 percent trans and 16.4 percent vinyl microstructure, typical of a lithium polymer prepared at this temperature with diethyl ether as a modifier. A Mn of 130,000 g/mol was measured by size exclusion chromatography with a Mw/Mn of 1.25. This represents over double the molecular weight expected from a monolithium catalyst, but would approximate the molecular weight of that obtained from a di-lithium initiator. Tin analysis showed 81 ppm.

Comparative Example II

The polymerization of comparative Example I was repeated using 2 mM of an approximately by 1M catalyst, prepared from the reaction of tributyltin chloride and lithium metal in tetrahydrofuran, according to the present invention. The living cement produced by the polymerization was a typical orange color and flowed readily. The addition of methanol had little effect on the viscosity and gave a clear colorless solution. Analysis indicated 23.4 percent cis, 37.9 percent trans and 38.6 percent vinyl microstructure typical to what would be expected from the polymerization conditions. The GPC showed a Mn of 55,200 g/mol and a Mw/Mn of 1.19. Tin analysis showed 860 ppm.

Comparative Example III (Polymer 12)

To a 2 gal reactor was added 0.76 lbs of a 33 percent styrene in hexane blend, 8.27 lbs of a 24.5 percent butadiene in hexane (1033 grams of monomers) and 16.5 mL of dry THF. Then 39.0 mL (13.42 millimoles) of a catalyst prepared according to Comparative Example I above, was added at 55° F. After 1.5 hours the temperature was increased to 70° F. and every subsequent 15 minutes by 10° F. until 120° F. was obtained. After an hour at this temperature the cement was cooled and added to isopropanol containing DBPC. Drum drying isolated the styrene/butadiene rubber which was compounded and cured. This polymer is reported as Polymer 12 in Table V hereinbelow.

Comparative Example IV (Polymer 13)

Another styrene/butadiene rubber was prepared as in Comparative Example III using n-butyl lithium as the catalyst with tetrahydrofuran as the modifier. The polymer was compounded, cured and tested, with the test data reported under Polymer 13 in Table V.

TABLE V

| Analysis of Polymers 12-13 | | |
|---|---|---|
| Polymer No. | 12 | 13 |
| Catalyst | $SnCl_2$ + BuLi | BuLi |
| % Vinyl PBD | 46 | 49.8 |
| % Styrene | 11.8 | 9.3 |
| Tg °C. | −56.6 | −57.1 |
| Mn X $10^{-3}$ | 183 | 168 |
| $ML_{1 + 4}$(100° C.) Gum | 51.2 | 88.9 |
| Compound | 144 | 153 |
| Tensile, psi | 2773 | 1920 |
| % Elongation | 335 | 281 |
| Rebound | | |
| @ 24°C. | 62.8 | 58.2 |
| @ 65°C. | 72 | 68.2 |
| % Δ tan δ | | |
| @ 24° C. | −18.3 | — |
| @ 65° C. | −24.7 | — |

It is apparent that the polymer compound produced according to the prior art (Polymer 12) produced a much smaller reduction in tan δ than is obtained by analogous polymers according to the present invention. For example, Polymers 3 and 7 according to the invention were prepared with a tin-containing initiator of the present invention and had no endcapping. These polymers showed significantly greater tan delta reduction characteristics than those according to the prior art.

It should now be clear from the foregoing examples and specification disclosure, that initiators according to the present invention are useful for the anionic polymerization of diene monomers. The resulting elastomeric polymers have a plurality of polymer chains, in which substantially each chain is provided with a tin atom derived from the initiator. These polymers exhibit improved hysteresis properties when compared to similar polymers prepared by similar means but lacking the tin-containing initiator. The elastomeric polymers may also be endcapped with another tin atom or other functionality, thus providing a difunctional polymer with still greater reduction of hysteresis. As a result, the vulcanizable compounds containing these polymers exhibit improved hysteresis properties which provides tread compounds improved rolling resistance in tires.

It is to be understood that the invention is not limited to the specific initiator reactants, organotin lithium initiators, monomers, terminators, polar coordinators or solvents disclosed herein, except as otherwise stated in the specification. Similarly, the examples have been provided merely to demonstrate practice of the subject invention and do not constitute limitations of the invention. Those skilled in the art may readily select other monomers and process conditions, according to the disclosure made hereinabove.

Thus, it is believed that any of the variables disclosed herein can readily be determined and controlled without departing from the scope of the invention herein disclosed and described. Moreover, the scope of the invention shall include all modifications and variations that fall within the scope of the attached claims.

We claim:

1. An elastomer having reduced hysteresis properties comprising:

a plurality of polymer molecules wherein substantially each said polymer molecule contains at least one tin atom and a lithium atom prior to quenching; wherein substantially each of said polymer molecules before termination has the general formula $R_3SnYLi$ where R is an organo group and Y is a polymer selected from the group consisting of diene homopolymers, monovinyl aromatic polymers, diene/monovinyl aromatic random copolymers and block copolymers.

2. An elastomer as in claim 1, wherein said organo group R is selected from the group consisting of alkyls having from about 1 to about 20 carbon atoms, cycloalkyls having from about 3 to about 20 carbon atoms, aryls having from about 6 to about 20 carbon atoms and aralkyl having from about 7 to about 20 carbon atoms.

3. An elastomer having reduced hysteresis properties made by anionically polymerizing a monomer solution containing at least one monomer selected from the group consisted of conjugated diene monomers having from about 4 to 12 carbon atoms, vinyl aromatic monomers having from about 8 to 18 carbon atoms and mixtures thereof, in the presence of an organic initiator containing tin; wherein substantially each polymer molecule of the elastomer contains a tin atom derived from said organic initiator; and, wherein substantially each of said polymer molecules before termination has the general formula $R_3SnYLi$ where R is an organo group and Y is a polymer selected from the group consisting of diene homopolymers, monovinyl aromatic polymers, diene/monovinyl aromatic random copolymers and block copolymers.

4. An elastomer as in claim 3, wherein said organo group R is selected from the group consisting of alkyls having from about 1 to about 20 carbon atoms, cycloalkyls having from about 3 to about 20 carbon atoms, aryls having from about 6 to about 20 carbon atoms and aralkyl having from about 7 to about 20 carbon atoms.

5. A elastomer as in claim 3, wherein said organic initiator comprises the reaction product of an organotin compound selected from the group consisting of triorgano substituted-tin halide compounds and hexaorgano substituted ditin compounds having a tin-tin bond, and lithium in the presence of a suitable solvent.

6. An elastomer as in claim 5, wherein said solvent is selected from the group consisting of tetrahydrofuran, tetramethylethylenediamine and diethylene glycol dimethyl ether.

7. An elastomer as in claim 5, wherein said reaction product is a triorgano substituted-tin lithium compound.

8. An elastomer as in claim 7, wherein the organo constituent of said triorgano substituted-tin lithium is selected from the group consisting of alkyls having from about 1 to about 20 carbon atoms, cycloalkyls having from about 3 to about 20 carbon atoms, aryls having from about 6 to about 20 carbon atoms and aralkyls having from about 7 to about 20 carbon atoms.

9. An elastomer as in claim 8, wherein said triorgano substituted-tin lithium is a trialkyl tin lithium.

10. An elastomer as in claim 9, wherein said trialkyl tin lithium is tributyl tin lithium.

11. An elastomer as in claim 3, wherein said monomer solution includes styrene and butadiene monomers in hexane.

12. An elastomer as in claim 5, wherein said hexaorgano substituted di-tin is hexabutyldi-tin.

13. An elastomer as in claim 3, wherein a plurality of said polymer molecules are endcapped with an endcapping agent.

14. An elastomer as in claim 13, wherein said endcapping agent is selected from the group consisting of tin tetrachloride, tributyl tin chloride, dibutyl tin dichloride and N,N'-dimethylethyleneurea.

15. A method of preparing an elastomer comprising the steps of:
   forming a solution of one or more anionically polymerizable monomers in a solvent, wherein said anionically polymerizable monomers are selected from the group consisting of conjugated dienes having from about 4 to about 12 carbon atoms, monovinyl aromatic monomers having 8 to 18 carbon atoms and trienes; and
   polymerizing said monomers in the presence of an organotin lithium initiator; wherein said elastomer comprises a plurality of polymer molecules, substantially each said molecule having a tin atom on one end and a lithium atom on the other end, prior to termination.

16. A method as in claim 15, wherein said solvent is hexane.

17. A method as in claim 15, wherein said organotin lithium initiator is a triorgano substituted-tin lithium compound.

18. A method as in claim 15, wherein said triorgano substituted-tin lithium compound is a trialkyl tin lithium compound wherein each alkyl has from 1 to about 20 carbon atoms.

19. A method as in claim 18, wherein said trialkyl tin lithium is tributyl tin lithium.

20. A method as in claim 15, wherein said step of polymerizing is further conducted in the presence of a polar coordinator selected from the group consisting of tetrahydrofuran, linear and cyclic oligomeric oxolanyl alkanes, tetramethylethylenediamine, di-piperidyl ethane, hexamethylphosphoramide, N-N'-dimethylpiperazine, diazabicyclooctane, dimethyl ether, diethyl ether and tributylamine.

21. A method as in claim 20, wherein said oligomeric oxolanyl alkane is 2-2'-di(tetrahydrofuryl) propane.

22. A method as in claim 15, wherein said plurality of polymer molecules are endcapped with an endcapping agent.

23. A method as in claim 22, wherein said endcapping agent is selected from the group consisting of tin tetrachloride, tributyl tin chloride, dibutyl tin dichloride and N,N'-dimethylethyleneurea.

24. An elastomer having reduced hysteresis properties made by anionically polymerizing a monomer solution containing at least one monomer selected from the group consisted of conjugated diene monomers having from about 4 to 12 carbon atoms, vinyl aromatic monomers having from about 8 to 18 carbon atoms and mixtures thereof, in the presence of an organic initiator containing tin; wherein substantially each polymer molecule of the elastomer contains a tin atom derived from said organic initiator; and,
   wherein said organic initiator comprises the reaction product of an organotin compound selected from the group consisting of triorgano substituted-tin halide compounds and hexaorgano substituted ditin compounds having a tin-tin bond, and lithium in the presence of a suitable solvent.

25. A vulcanizable elastomeric compound having reduced hysteresis properties comprising:
   an elastomer comprising a plurality of polymer molecules wherein substantially each said polymer molecule contains at least one tin atom and a lithium atom prior to quenching, wherein substantially each of said polymer molecules before termination has the general formula $R_3SnYLi$ where R is an organo group and Y is a polymer selected from the group consisting of diene homopolymers, monovinyl aromatic polymers, diene/monovinyl aromatic random copolymers and block copolymers; and,
   from about 20 to about 100 parts by weight of carbon black, per 100 parts of said elastomer.

26. An improved tire having decreased rolling resistance resulting from a treadstock containing a vulcanizable elastomeric compound comprising:
   an elastomer comprising a plurality of polymer molecules wherein substantially each said polymer molecule contains at least one tin atom and a lithium atom prior to quenching, wherein substantially each of said polymer molecules before termination has the general formula $R_3SnYLi$ where R is an organo group and Y is a polymer selected from the group consisting of diene homopolymers, monovinyl aromatic polymers, diene/monovinyl aromatic random copolymers and block copolymers; and,
   from about 20 to about 100 parts by weight of carbon black, per 100 parts of said elastomer.

* * * * *